(12) United States Patent
Clendennen et al.

(10) Patent No.: US 7,872,047 B2
(45) Date of Patent: Jan. 18, 2011

(54) ESTERS OF LONG-CHAIN ALCOHOLS AND PREPARATION THEREOF

(75) Inventors: Stephanie Kay Clendennen, Kingsport, TN (US); Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 554 days.

(21) Appl. No.: 12/028,240

(22) Filed: Feb. 8, 2008

(65) Prior Publication Data

US 2009/0203779 A1   Aug. 13, 2009

(51) Int. Cl.
| | |
|---|---|
| A61K 8/37 | (2006.01) |
| A61K 31/215 | (2006.01) |
| A61Q 19/00 | (2006.01) |
| A61P 17/00 | (2006.01) |
| A61F 2/00 | (2006.01) |
| C12N 9/20 | (2006.01) |
| C12N 9/50 | (2006.01) |
| C07C 69/76 | (2006.01) |

(52) U.S. Cl. .................. 514/549; 424/400; 435/219; 560/51

(58) Field of Classification Search .................. None
See application file for complete search history.

(56) References Cited

U.S. PATENT DOCUMENTS

| | | | |
|---|---|---|---|
| 4,271,083 | A | 6/1981 | Morimoto et al. |
| 4,407,757 | A | 10/1983 | Morimoto et al. |
| 6,756,045 | B1 | 6/2004 | Neudecker et al. |
| 2004/0197282 | A1 | 10/2004 | Neudecker et al. |
| 2005/0175559 | A1 | 8/2005 | DiNardo et al. |
| 2005/0197407 | A1 | 9/2005 | DiNardo et al. |

FOREIGN PATENT DOCUMENTS

| | | |
|---|---|---|
| EP | 1 449 511 A1 | 8/2004 |
| EP | 1 702 614 A1 | 9/2006 |
| WO | WO 2005/070370 A1 | 8/2005 |
| WO | WO 2009/202586 A2 | 2/2009 |

OTHER PUBLICATIONS

Notification of Transmittal of the International Search Report and the Written Opinion of the International Searching Authority, or the Declaration date of mailing Jan. 26, 2009 received in International Patent Application No. PCT/US2008/009386.
Pignatello, R. et al.; "A calorimetric evaluation of the interaction of amphiphilic prodrugs of idebenone with a biomembrane model"; Journal of Colloid and Interface Science; 299; (2006); pp. 626-635.
Yu, C. A. et al.; "Syntheses of Biologically Active Ubiquinone Derivatives"; Biochemistry; 21; 1982; pp. 4096-4101.
Bartee, S.D. et al.; "Effects of antioxidants on the oxidative stability of oils containing arachidonic, docosapentaaenoic and docosahexaenoic acids"; *J Amer Oil Chem Soc*; 2007; 84: 363-68.
Demarco et al., *Biochem. Pharmacol.*; 2002; 64; 1503-1512.
Kojima, Hajime et al.; "Evaluation of skin irritation in a reconstituted human dermal model (3-D model) using water insoluble fatty acids, fatty alcohols and hydrocarbons"; Altern. Animal Test. Experiment; 1998; pp. 201-210; Volume-Issue No. 5.
McDaniel, D. H. et al.; "Clinical efficacy assessment in photodamaged skin of 0.5% and 1.0% idebenone"; Journal of Cosmetic Dermatology; 2005; pp. 167-173; Volume-Issue No. 4; Blackwell Publishing.
Narayanan, S. et al.; "Scavenging properties of metronidazole on free oxygen radicals in a skin lipid model system"; *J Pharm Pharmacol*; Aug. 2007; 59(8):1125-30.
Schürer, N.Y.; "Implementation of fatty acid carriers to skin irritation and the epidermal barrier"; Contact Dermatitis; 2002; pp. 199-205; Volume-Issue No. 47; Blackwell Munksgaard; Denmark.
Notification of Transmittal of the International Search Report and the Written Opinion of the International Searching Authority, or the Declaration date of mailing Jun. 26, 2009 received in corresponding International Application No. PCT/US2009/000404.
Co-pending U.S. Appl. No. 11/890,974, filed Aug. 8, 2007, Clendennen and Boaz; now U. S. Publication No. 2009-0042271.

*Primary Examiner*—Robert A Wax
*Assistant Examiner*—Danah Al-Awadi
(74) *Attorney, Agent, or Firm*—Brett L Nelson; Bernard J. Graves, Jr.

(57) ABSTRACT

Disclosed is a composition and methods of treating a skin condition. The ester includes an ester and a dermatologically acceptable carrier. The ester is represented by the general formula 1:

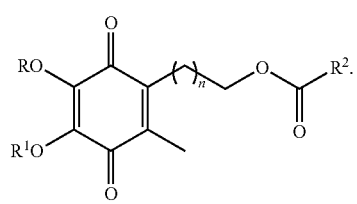

10 Claims, No Drawings

ESTERS OF LONG-CHAIN ALCOHOLS AND PREPARATION THEREOF

BACKGROUND OF THE INVENTION

Long-chain alcohols have a number of uses in cosmetics and personal care. Long chain alcohols such as behenyl alcohol are useful as emollients to make skin smoother and prevent moisture loss. Other alcohols are useful as active ingredients. One such example is idebenone, which is a potent anti-oxidant which has been shown to reduce skin roughness and fine lines and wrinkles, and also to improve photodamaged skin (McDaniel, D. H.; Neudecker, B. A.; Dinardo, J. C.; Lewis II, J. A.; Maibach, H. I. *Journal of Cosmetic Dermatology* 2005, 4,167-173). This material has also been claimed to induce protective and regenerative effects (U.S. Pat. No. 6,756,045), reduce skin hyperpigmentation (US Patent Publication 2005/0175559), and to reduce irritation and/or inflammatory reaction in human skin (US Patent Application Publication 2005/0197407). Ester derivatives of idebenone may improve the physical properties of this orange solid. In addition, esters of idebenone with fatty acids will hydrolyze in the skin to afford idebenone along with the fatty acid derivative which may also have positive benefits.

The classical chemical preparation of esters such as idebenone involves either the reaction of the alcohol with an acid, acid chloride, or acid anhydride. These methods often use either harsh reagents or high temperatures, which can cause difficulties if either the alcohol or the acid derivative is unstable.

There have been reports of short-chain esters of idebenone and similar molecules. U.S. Pat. No. 4,271,083 reports alkyl esters of idebenone and similar molecules where the alkyl ester has 1-4 carbon atoms. U.S. Pat. No. 4,407,757 describes acetate esters of idebenone and similar molecules. U.S. Pat. No. 6,756,045 describes hydrophilic esters of idebenone, particularly sulfonic acid esters. None of these references prepared these materials by enzymatic means.

None of the references describe a derivative of idebenone with a long-chain fatty acid, which may be more physiologically compatible and less irritating to skin than a shorter chain fatty acid (Schurer, 2002, Contact Dematitis 47: 199; Kojima et al., 1998, Altern Animal Test. Exper. 5: 201).

BRIEF SUMMARY OF THE INVENTION

A first embodiment according to the present invention concerns a composition, comprising an ester and a dermatologically acceptable carrier, wherein the ester is represented by the general formula 1:

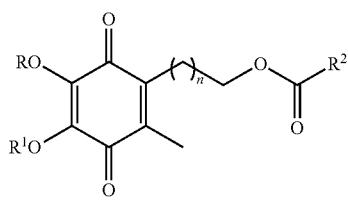

wherein

R and $R^1$ are independently a $C_1$-$C_4$ alkyl, $R^2$ is selected from the group consisting of a $C_5$-$C_{22}$ alkyl, a $C_5$-$C_{22}$ alkenyl, a $C_5$-$C_{20}$ dienyl, a $C_6$-$C_{22}$ trienyl, a $C_8$-$C_{22}$ tetraenyl and mixtures thereof, and n is 2-12.

Another embodiment concerns a method for treating a skin condition comprising applying to skin an effective amount of a composition comprising an ester and a dermatologically acceptable carrier, wherein the ester is represented by the general formula 1:

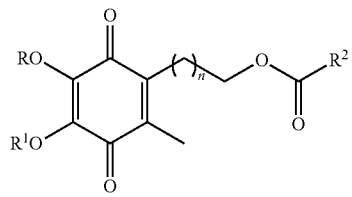

wherein

R and $R^1$ are independently a $C_1$-$C_4$ alkyl, $R^2$ is selected from the group consisting of a $C_5$-$C_{22}$ alkyl, a $C_5$-$C_{22}$ alkenyl, a $C_5$-$C_{20}$ dienyl, a $C_6$-$C_{22}$ trienyl, a $C_8$-$C_{22}$ tetraenyl and mixtures thereof, and n is 2-12.

DETAILED DESCRIPTION

The present invention concerns a series of novel esters of long-chain alcohols and compositions containing the esters which esters are represented by the general formula 1:

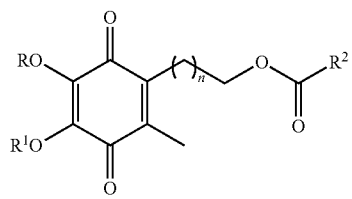

wherein

R and $R^1$ are selected from branched- and straight-chain $C_1$-$C_4$ alkyl, $R^2$ is selected from substituted and unsubstituted, branched- and straight-chain saturated $C_5$-$C_{22}$ alkyl, substituted and unsubstituted, branched- and straight-chain $C_5$-$C_{22}$ alkenyl, substituted and unsubstituted, branched- and straight-chain $C_5$-$C_{20}$ dienyl, substituted and unsubstituted, branched- and straight-chain $C_6$-$C_{22}$ trienyl, and substituted and unsubstituted, branched- and straight-chain $C_8$-$C_{22}$ tetraenyl or mixtures thereof, and n is 2-12.

The alkyl, alkenyl, dienyl, trienyl, and tetraenyl groups which may be represented by $R^2$ may be straight- or branched-chain aliphatic hydrocarbon radicals containing up to about 20 carbon atoms and may be substituted, for example, with one to three groups selected from $C_1$-$C_6$-alkoxy, cyano, $C_2$-$C_6$-alkoxycarbonyl, $C_2$-$C_6$-alkanoyloxy, hydroxy, aryl, heteroaryl, thiol, thioether, and halogen. The terms "$C_1$-$C_6$-alkoxy", "$C_2$-$C_6$-alkoxycarbonyl", and "$C_2$-$C_6$-alkanoyloxy" are used to denote radicals corresponding to the structures —$OR^3$, —$CO_2R^3$, and —$OCOR^3$, respectively, wherein $R^3$ is $C_1$-$C_6$-alkyl or substituted $C_1$-$C_6$-alkyl.

Examples of the compounds of the invention include those represented by formula 1 wherein acyl group $R^2$—CO is linoleoyl, stearoyl, linolenoyl, conjugated linoleoyl, palmoyl, and oleoyl or mixtures thereof.

The esters can be prepared by reacting an alcohol represented by 2

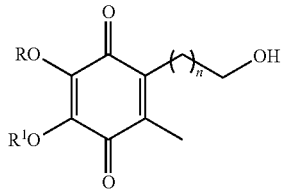

with a long-chain acid $R^2COOH$ or long-chain ester $R^2COOR^4$ in the presence of an inert solvent and an enzyme with or without methods for the removal of water wherein R, $R^1$, and $R^2$ are as defined above and $R^4$ is a straight or branched $C_1$-$C_4$ alkane or alkene. For the purposes of the present invention, a long-chain acid or a long-chain ester would include those acids or esters having chains of 5 carbon atoms or more.

The straight or branched $C_1$-$C_4$ alkyl or alkenyl group represented by $R^4$ may be chosen from methyl, ethyl, n-propyl, i-propyl, n-butyl, s-butyl, vinyl, 1-propenyl, 2-propenyl, 2-butenyl and the like.

The process is carried out in an inert solvent chosen from cyclic or acyclic ether solvents such as diethyl ether, diisopropyl ether, tert-butyl methyl ether, or tetrahydrofuran, aromatic hydrocarbons such as benzene, toluene, or xylene, aliphatic or alicyclic saturated or unsaturated hydrocarbons such as hexane, heptane, cyclohexane, or limonene, halogenated hydrocarbons such as dichloromethane, dichloroethane, dibromoethane, tetrachloroethylene, or chlorobenzene, polar aprotic solvents such as acetonitrile, dimethyl formamide, or dimethyl sulfoxide, or mixtures thereof. Examples of acceptable solvents include toluene, limonene, and acetonitrile. The process may be carried out at a temperature between about −100° C. and the boiling point of the solvent, or between about 0-60° C., or even between about 20-50° C. The amount of long-chain acid or long-chain ester may be between 0.85 and 20 equivalents based on the amount of the alcohol represented by 2, or between 1 and 10 equivalents based on the amount of alcohol. The enzyme used in the process is chosen from a protease, a lipase, or an esterase. For example, lipases may be used and may be in the form of whole cells, isolated native enzymes, or immobilized on supports. Examples of these lipases include but are not limited to Lipase PS "Amano" (from *Pseudomonas* sp), Lipase PS-C "Amano" (from *Psuedomonas* sp immobilized on ceramic), Lipase PS-D "Amano" (from *Pseudomonas* sp immobilized on diatomaceous earth), LipoPrime® 50T, Lipozyme® TL IM, or Novozym® 435 (from *Candida antarctica* immobilized on acrylic resin).

The process may optionally be carried out in the presence of various addenda chosen from molecular sieves or ion exchange resins. For example, 3A, 4A, or 5A molecular sieves can be used.

The product of the process may be isolated using methods known to those of skill in the art, e.g., extraction, filtration, or crystallization. The product 1 may be purified if necessary using methods known to those of skill in the art, e.g., extraction, chromatography, distillation, or crystallization.

The esters according to the present invention can be used in compositions, such as cosmetic compositions, skin care compositions and the like. The compositions can be useful, for example, for reducing skin roughness, fine lines and wrinkles, improving photodamaged skin, regenerating skin, reducing skin hyperpigmentation, and reducing irritation and/or inflammatory reaction in skin.

Typical cosmetic and/or skin care compositions of the invention contain at least 0.001% by weight of the esters according to the present invention. For example, the compositions can contain from about 0.001% to about 10.0% by weight or from about 0.01% to about 5.0% by weight of the esters according to the present invention. Lower concentrations may be employed for less pronounced conditions, and higher concentrations may be employed with more acute conditions. Suggested ranges also depend upon any adjunct ingredients employed in the compositions.

The cosmetic and skin care compositions of the invention may also contain other skin conditioning ingredients in addition to esters. Such other ingredients are known to those of skill in the art.

Typically, topical application to skin sites is accomplished in association with a carrier. Where employed, the carrier is inert in the sense of not bringing about a deactivation or oxidation of active or adjunct ingredient(s), and in the sense of not bringing about any adverse effect on the skin areas to which it is applied. For example, the compounds according to the present invention are applied in admixture with a dermatologically acceptable carrier or vehicle (e.g., as a lotion, cream, ointment, soap, stick, or the like) so as to facilitate topical application and, in some cases, provide additional beneficial effects as might be brought about, e.g., by moisturizing of the affected skin areas. Many preparations are known in the art, and include lotions containing oils and/or alcohols and emollients such as olive oil, hydrocarbon oils and waxes, silicone oils, other vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids.

EXAMPLES

This invention can be further illustrated by the following examples, although it will be understood that these examples are included merely for purposes of illustration and are not intended to limit the scope of the invention unless otherwise specifically indicated.

Example 1

Preparation of Idebenone Linoleate
(1a)(EX00011-037)

Idebenone (2a, $R=R^1=Me$, n=9; 547 mg; 1.6 mmol) was dissolved in 10 mL of toluene. Linoleic acid (2.18 g; 4.9 equiv) was added followed by 641 mg of 4 A molecular sieves and 309 mg of Novozym® 435. The reaction mixture was stirred at ambient temperature for 2 days, at which point tlc analysis (1:1 ethyl acetate:heptane eluant) indicated no remaining idebenone. The solids were removed by filtration and the precipitate washed with toluene. The combined filtrate and washes were concentrated at reduced pressure. The residue was dissolved in heptane (22 mL) and washed with a mixture of 11 mL of methanol and 11 mL of 10% aqueous potassium carbonate. The organic layer was further washed with a mixture of 11 mL of methanol, 4 mL of saturated sodium bicarbonate, and 7 mL of water. The organic layer was then dried with sodium sulfate and concentrated to afford 0.84 g (87%) of 1a (R=R$^1$=Me, n=9).

$^1$H NMR (CDCl3) δ 5.40-5.30 (m, 4H); 4.049 (t, 2H, J=6.87 Hz); 3.988 (s, 6H); 2.768 (t, 2H, J=5.77 Hz); 2.45 (m, 2H); 2.288 (t, 2H, J=7.42 Hz); 2.08-2.01 (m, 3H); 2.009 (s, 3H); 1.64-1.57 (m, 3H); 1.40-1.29 (m, 30H); 0.89 (t, 3H, J=6.60 Hz).

Example 2

Preparation of Idebenone Conjugated Linoleate (1b)(EX00011-037)

Idebenone (2a; 499 mg; 1.48 mmol) was dissolved in 10 mL of toluene. Conjugated linoleic acid (Tonalin® FFA; 2.07 g; 5 equiv) was added followed by 500 mg of 4 A molecular sieves and 300 mg of Novozym® 435. The reaction mixture was stirred at ambient temperature for 2 days, at which point tlc analysis (1:1 ethyl acetate:heptane eluant) indicated a small amount of idebenone. Additional 4 A molecular sieves were added and the mixture was stirred for an additional 2 days, at which point tlc analysis indicated no remaining idebenone. The solids were removed by filtration and the precipitate washed with toluene. The combined filtrate and washes were concentrated at reduced pressure. The residue was dissolved in heptane (50 mL) and washed twice with a 1:1 mixture of methanol and 10% aqueous potassium carbonate (50 mL, then 20 mL). The organic layer was further washed with a mixture of 15 mL of methanol, 5 mL of saturated sodium bicarbonate, and 10 mL of water. The organic layer was then dried with sodium sulfate and concentrated to afford 850 mg (96%) of 1b.

$^1$H NMR (CDCl3) δ 6.33-6.24 (m,1H); 5.935 (t,1H, J=11.0 Hz); 5.60-5.60 (m, 1H); 5.35-5.26 (m, 1H); 4.049 (t, 2H, J=6.60 Hz); 3.988 (s, 3H); 3.986 (s, 3H); 2.445 (t, 2H, J=6.87 Hz); 2.285 (t, 2H, J=7.42 Hz); 2.18-2.05 (m, 3H); 2.009 (s, 3H); 1.62-1.56 (m, 5H); 1.30-1.23 (m, 30H); 0.91-0.86 (m, 3H).

Example 3

Preparation of Idebenone Ester with Pamolyn 200 Linoleic Acid (1c)(EX00011-037)

Idebenone (2a; 501 mg; 1.48 mmol) was dissolved in 10 mL of toluene. Pamolyn 200® linoleic acid (2.07 g; 5 equiv) was added followed by 500 mg of 4 A molecular sieves and 300 mg of Novozym® 435. The reaction mixture was stirred at ambient temperature for 2 days, at which point tlc analysis (1:1 ethyl acetate:heptane eluant) indicated a small amount of idebenone. Additional 4 A molecular sieves were added but no change was observed by tlc. The solids were removed by filtration and the precipitate washed with toluene. The combined filtrate and washes were concentrated at reduced pressure. The residue was dissolved in heptane (50 mL) and washed with a 1:1 mixture of methanol and 10% aqueous potassium carbonate (50 mL). The organic layer was further washed with a mixture of 15 mL of methanol, 5 mL of saturated sodium bicarbonate, and 10 mL of water. The organic layer was then dried with sodium sulfate and concentrated to afford 798 mg (90%) of 1b.

Example 4

Preparation of Idebenone Octanoate (1d)(EX00011-037)

Idebenone (2a; 500 mg; 1.48 mmol) was dissolved in 10 mL of toluene. Octanoic acid (1.07 g; 5 equiv) was added followed by 500 mg of 4 A molecular sieves and 300 mg of Novozym® 435. The reaction mixture was stirred at ambient temperature for 2 days, at which point tlc analysis (1:1 ethyl acetate:heptane eluant) indicated no idebenone. The solids were removed by filtration and the precipitate washed with toluene. The combined filtrate and washes were concentrated at reduced pressure. Concentration in vacuo afforded 630 mg (92%) of 1d.

$^1$H NMR (CDCl3) δ 4.051 (t, 2H, J=6.87 Hz); 3.990 (s, 3H); 3.987 (s, 3H); 2.446 (t, 2H, J=7.15 Hz); 2.289 (t, 2H, J=7.42 Hz); 2.010 (s, 3H); 1.61-1.57 (m, 5H); 1.33-1.28 (m, 30H); 0.878 (t, 3H, J=6.60 Hz).

Example 5

Oxidation of skin lipids can contribute to an aged appearance and other undesirable effects on skin condition. A simple skin lipid model (based on fatty acids found in skin) can be used to evaluate and predict the topical effectiveness of different compounds to inhibit skin lipid oxidation and improve the condition of skin (Narayanan, S.: Hunerbein, A.: Getie, M.; Jackel, A.; Neubert, R. H. Scavenging properties of metronidazole on free oxygen radicals in a skin lipid model system. *J Pharm Pharmacol.* 2007 August;59(8):1125-30).
).

Lipid oxidation can be measured by a number of analytical methods. An accelerated oxidation test such as the Oxidative Stability Index (OSI) is accepted as a method for determining both oxidative stability of lipids as well as antioxidant effectiveness (Bartee, S. D.; Kim, H. J.; Min, D. B. Effects of antioxidants on the oxidative stability of oils containing arachidonic, docosapentaaenoic and docosahexaenoic acids. *J Amer Oil Chem Soc* 2007 84: 363-68.; Official methods and recommended practices of the AOCS, 5$^{th}$ Edition, AOCS 1998).

In this example, the OSI method was used to assess the antioxidant activity of idebenone esters by measuring their ability to inhibit lipid oxidation in a mixture of fatty acids that are present in skin lipids. The composition of the simple skin lipid model tested is 74% linoleic acid; 21% oleic acid; 4% linolenic acid. The simple skin lipid model includes a large proportion of polyunsaturated and unsaturated fatty acids, which are prone to oxidation.

The untreated sample was composed of the simple skin lipid model (fatty acid mixture). The treated samples were prepared by dissolving the test materials in the simple skin lipid model at 1 or 2 wt % at room temperature. The treated and untreated lipid matrices were oxidized by heating the test solutions to 80° C. and bubbling air through the samples. The OSI (induction period in hours) was determined using an Oxidative Stability Instrument (Omnion, Inc. Rockville Md.) and the method of Bartee et al., 2007. Untreated and treated samples were tested in triplicate, and the average and standard deviation are included in Table 1. The OSI (induction period in hours) was also estimated for oxidation at 35° C. (simulating skin surface temperature) using the software supplied with the instrument.

TABLE 1

| Sample | Avg. OSI (stdev) Hours at 80° C. | Calculated OSI Hours at 35° C. |
|---|---|---|
| Untreated skin lipid model matrix (SLMM) | 1.07 (0.03) | 24.1 |
| 1 wt % (27 mM) idebenone in SLMM | 2.77 (0.14) | 62.3 |
| 1 wt % (15 mM) idebenone linoleate in SLMM | 2.50 (0.54) | 56.2 |
| 2 wt % (30 mM) idebenone linoleate in SLMM | 3.22 (0.67) | 72.4 |

Treating the simple skin lipid model matrix with either 1% idebenone (a known potent antioxidant) or 1% or 2% idebenone linoleate significantly delayed the onset of lipid oxidation over the untreated control (p<0.01). The antioxidant treatments are not significantly different from one another, indicating that long chain esters of idebenone are effective antioxidants in a skin lipid model system.

Example 6

The preliminary toxicological effects of the esters of the invention were examined using a 3-[4,5-dimethylthiazol-2-yl]-2,5-diphenyl tetrazolium bromide (MTT) spectrophotometric cell viability assay with mouse melanocytes (example reference, DeMarco et al., *Biochem. Pharmacol.* 2002, 64,1503-1512). Melanocytes (B16:F10 mouse melanoma cells) were purchased from ATCC (American Type Culture Collection; Manassas, Va.). Cells were grown at 37° C. in DMEM (Dulbecco's Modified Eagle's Medium) without phenol red, and in the presence of 10% FCS (fetal bovine serum) and 1% antibiotics. Upon becoming confluent (~90%), cells were detached with trypsin-EDTA and counted. Cells ($5 \times 10^5$ cells/well) were then plated into 96 well plates (Corning/Costar #3595) using a volume of 100±1 μL medium/well.

Twenty-four hours after initially plating, stock solutions of idebenone and idebenone linoleate were freshly prepared in DMSO. The stock solution was diluted in culture medium to give concentrations of 2, 20, 200, and 1000 μM; DMSO concentrations were consistently kept at 0.2%. Next, 100 μL of each dilution was added to the existing 100 μL/well culture and 1000 μM per well with 0.1% DMSO. Eight replicates were run for each dilution.

At 24 hours post-dose, 10% MTT solution (20 uL; 5.0 mg/mL in DMEM without phenol red) was added to each well. The plate was incubated for 2 hours at ~37° C. Medium was carefully removed and MTT solvent solution (200 μL; 0.1 N HCl in anhydrous isopropanol) was added to each well. Mitochondrial dehydrogenases (reductases) from viable cells cleave the tetrazolium ring, yielding purple MTT formazan crystals. For a given time point, the number of viable cells correlates with MTT formazan production. Using a Molecular Devices Spectra Max 340 (Sunnyvale, Calif.), the 96-well plate was shaken (10 minutes) and the amount of MTT formazan was subsequently read using an absorbance wavelength of 570 nm with a subtracted background absorbance read at 690 nm. The data for cell viability for idebenone and idebenone linoleate are tabulated below. Idebenone was readily cytotoxic to the melanocytes at ≧100 uM; whereas, idebenone linoleate was not cytotoxic to the melanocytes at all tested concentrations, suggesting that long chain esters of idebenone may have improved tolerance (lower cytotoxicity and irritation) in biological systems.

| Concentration | Idebenone cell viability | Idebenone linoleate cell viability |
|---|---|---|
| 0 | 100% | 100% |
| 1 μM | 104% | 98% |
| 10 μM | 93% | 98% |
| 100 μM | 27% | 93% |
| 500 μM | 2% | 95% |

The invention has been described in detail with particular reference to preferred embodiments thereof, but it will be understood that variations and modifications can be effected within the spirit and scope of the invention.

We claim:

1. A composition, comprising an ester and a dermatologically acceptable carrier, wherein the ester is represented by the general formula 1:

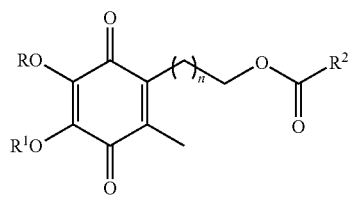

wherein
R and $R^1$ are independently a $C_1$-$C_4$ alkyl,
$R^2$ is selected from the group consisting of a $C_{11}$-$C_{22}$ alkyl, a $C_5$-$C_{22}$ alkenyl, a $C_5$-$C_{20}$ dienyl, a $C_6$-$C_{22}$ trienyl, a $C_8$-$C_{22}$ tetraenyl and mixtures thereof, and
n is 2-12.

2. The composition according to claim 1, wherein the ester is present in an amount of at least 0.001% by weight.

3. The composition according to claim 2, wherein the ester is present in an amount of from about 0.001% to about 10% by weight.

4. The composition according to claim 3, wherein the ester is present in an amount of from about 0.01% to about 5.0% by weight.

5. The composition according to claim 1, wherein the alkyl, alkenyl, dienyl, trienyl, and tetraenyl group of $R^2$ is an aliphatic hydrocarbon radical containing up to about 22 carbon atoms.

6. The composition according to claim 5, wherein the aliphatic hydrocarbon contain up to 22 carbon atoms is substituted with one to three groups selected from the group consisting of $C_1$-$C_6$-alkoxy, cyano, $C_2$-$C_6$-alkoxycarbonyl, $C_2$-$C_6$-alkanoyloxy, hydroxy, aryl, heteroaryl, thiol, thioether, and halogen.

7. The composition according to claim 1, wherein an acyl group $R^2$—CO is selected from the group consisting of linoleoyl, stearoyl, linolenoyl, conjugated linoleoyl, palmoyl, oleoyl and mixtures thereof.

8. The composition according to claim 1, wherein the composition is a lotion, a cream, a gel, an ointment, a soap, or a stick.

9. A method for treating a skin condition comprising applying an effective amount of the composition according to claim 1 to skin.

10. The method according to claim 9, wherein said skin condition is selected from the group consisting of skin roughness, skin wrinkles, photodamaged skin, skin hyperpigmentation, skin irritation and skin inflammatory reaction.

* * * * *